(12) United States Patent
Cheng et al.

(10) Patent No.: US 8,347,884 B2
(45) Date of Patent: Jan. 8, 2013

(54) BRUSHLESS FAN MOTOR AND POSITIVE AIRWAY PRESSURE BREATHING APPARATUS USING THE SAME

(75) Inventors: Feng-Kun Cheng, Hsinchu County (TW); Chih-Yang Hsiao, Hsinchu County (TW)

(73) Assignee: Lead Data Inc., Hsinchu Hsien (TW)

( * ) Notice: Subject to any disclaimer, the term of this patent is extended or adjusted under 35 U.S.C. 154(b) by 128 days.

(21) Appl. No.: 13/099,799

(22) Filed: May 3, 2011

(65) Prior Publication Data
US 2012/0180792 A1 Jul. 19, 2012

(30) Foreign Application Priority Data
Jan. 14, 2011 (TW) .............................. 100200925 U

(51) Int. Cl.
*A61M 11/00* (2006.01)
(52) U.S. Cl. ......... 128/204.18; 310/154.01; 310/156.01; 417/423.1
(58) Field of Classification Search ............. 128/204.18; 310/154.01, 154.02, 154.21, 154.25, 156.01; 417/423.1, 423.12
See application file for complete search history.

(56) References Cited

U.S. PATENT DOCUMENTS

| | | | | |
|---|---|---|---|---|
| 4,804,873 A | * | 2/1989 | Shiraki et al. | 310/67 R |
| 4,891,537 A | * | 1/1990 | Shiraki et al. | 310/68 B |
| 4,894,572 A | * | 1/1990 | Shiraki | 310/68 B |
| 7,567,001 B2 | * | 7/2009 | Kasai et al. | 310/71 |

* cited by examiner

*Primary Examiner* — Steven Douglas
(74) *Attorney, Agent, or Firm* — WPAT PC; Justin King

(57) ABSTRACT

A brushless fan motor includes a case, a tubular part disposed in the case and fixed at a bottom of the case, at least a bearing disposed in the tubular part, a toric coil surrounding the tubular part, and a rotating assembly. The rotating assembly includes a turntable, a rotating shaft, a loading ring, a permeability metal element and a toric radial magnet. The turntable has a top surface and fan blades disposed on the top surface. The rotating shaft is disposed through the bearing and connected to the turntable. The loading ring connected to the turntable surrounds the toric coil. The permeability metal element includes an annular part fixed at an inner wall of the loading ring. The toric radial magnet is fixed at an inner wall of the annular part. A positive airway pressure breathing apparatus using the brushless fan motor is also provided.

10 Claims, 5 Drawing Sheets

BRUSHLESS FAN MOTOR AND POSITIVE AIRWAY PRESSURE BREATHING APPARATUS USING THE SAME

FIELD OF THE INVENTION

The present invention relates to a motor, and more particularly to a brushless fan motor and a positive airway pressure breathing apparatus using the same.

BACKGROUND OF THE INVENTION

With the progress of medical science and technical art, living quality of modern people is improved day by day. For example, sleeping quality of a patient with obstructive sleep apnea syndrome (OSAS) can be improved by using a positive airway pressure breathing apparatus. The positive airway pressure breathing apparatus needs a fan motor to provide air to a user, so the fan motor is one of key members of the positive airway pressure breathing apparatus.

FIG. 1 is a three dimensional cross sectional view of a conventional brushless fan motor of a positive airway pressure breathing apparatus, and FIG. 2 is a three dimensional exploded view of FIG. 1. Referring to FIGS. 1 and 2, a brushless fan motor 1 is disclosed in U.S. Pat. No. 6,960,854. The brushless fan motor 1 includes an upper case 2 and a lower case 3 combined with the upper case 2. A bearing 13 is disposed in the lower case 3, and a bearing 14 is disposed in the upper case 2. A rotating shaft 4 is disposed through the bearings 13 and 14. A fan blade turntable 7 is fixed at the rotating shaft 4 to be rotated with the rotating shaft 4. A toric magnet 5 is fixed at the rotating shaft 4, and the toric magnet 5 is surrounded by a toric coil 6.

When a current is applied to the toric coil 6, an induced electromagnetic field is generated to rotate the toric magnet 5, and the fan blade turntable 7 is thereby rotated with the toric magnet 5. An air flow is generated when the fan blade turntable 7 is rotated. The air can be output from an outlet 25 to a user through a pipe (not shown) connected with the outlet 25.

However, in the conventional technique, the bearings 13 and 14 are respectively disposed at the lower case 3 and the upper case 2. Due to assembling tolerance between the upper case 2 and the lower case 3, the bearings 13 and 14 may not be positioned in the same central axis. This results in an eccentric rotation when the rotating shaft 4 is rotated, and therefore, huge noise is generated when the positive airway pressure breathing apparatus is worked.

SUMMARY OF THE INVENTION

The present invention provides a brushless fan motor to reduce noise.

The present invention further provides a positive airway pressure breathing apparatus to reduce noise.

The present invention provides a brushless fan motor including a case, a tubular part, at least a bearing, a toric coil and a rotating assembly. The case has a top, a bottom and a side located between the bottom and the top. The top of the case has an inlet disposed thereon, and the side wall has an outlet disposed thereon. The tubular part is disposed in the case, and an end of the tubular part is fixed at the bottom. The bearing is disposed in the tubular part, and the toric coil surrounds the tubular part. The rotating assembly includes a turntable, a rotating shaft, a loading ring, a permeability metal element and a toric radial magnet. The turntable has a top surface facing the top of the case and a plurality of fan blades disposed on the top surface. The rotating shaft is disposed through the bearing, and an end of the rotating shaft is connected to the turntable. The loading ring is connected to the turntable and surrounds the toric coil. Moreover, the permeability metal element has an annular part fixed at an inner wall of the loading ring. The toric radial magnet is fixed at an inner wall of the annular part of the permeability metal element.

In an embodiment of the present invention, the case includes a base and a cover, the cover comprises the top, the base comprises the bottom, and the side wall and the outlet are composed of a portion of the base and a portion of the cover.

In an embodiment of the present invention, the turntable and the loading ring are integrated into one piece.

In an embodiment of the present invention, the brushless fan motor further includes a flow guiding member fixed at the bottom of the case and surrounding the loading ring of the rotating assembly.

In an embodiment of the present invention, the flow guiding member includes a toric side wall and a toric platform. The toric side wall surrounds the loading ring of the rotating assembly, and a bottom end of the toric side wall is fixed at the bottom of the case. The toric platform is extended from a top end of the toric side wall toward outside of the toric side wall.

The present invention further provides a positive airway pressure breathing apparatus including a box, the above-mentioned brushless fan motor, a power control module and a circuit board assembly. The box has a fist air hole and a second air hole. The circuit board assembly, the power control module and the brushless fan motor are disposed in the box. The circuit board assembly is electrically connected to the power control module, and the power control module is electrically connected to the brushless fan motor. The inlet of the brushless fan motor is communicated with the fist air hole, and the outlet of the brushless fan motor is communicated with the second air hole.

In the brushless fan motor of the present invention, each bearing is disposed at the tubular part which is fixed at the bottom of the case, thereby preventing a central axis of the bearing from being tilted. Such that, an eccentric rotation of the rotating shaft can be avoided so as to reduce noise of the brushless fan motor of the present invention. Moreover, noise of the positive airway pressure breathing apparatus of the present invention can be reduced because the positive airway pressure breathing apparatus is equipped with the brushless fan motor.

BRIEF DESCRIPTION OF THE DRAWINGS

The above objects and advantages of the present invention will become more readily apparent to those ordinarily skilled in the art after reviewing the following detailed description and accompanying drawings, in which.

DETAILED DESCRIPTION

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
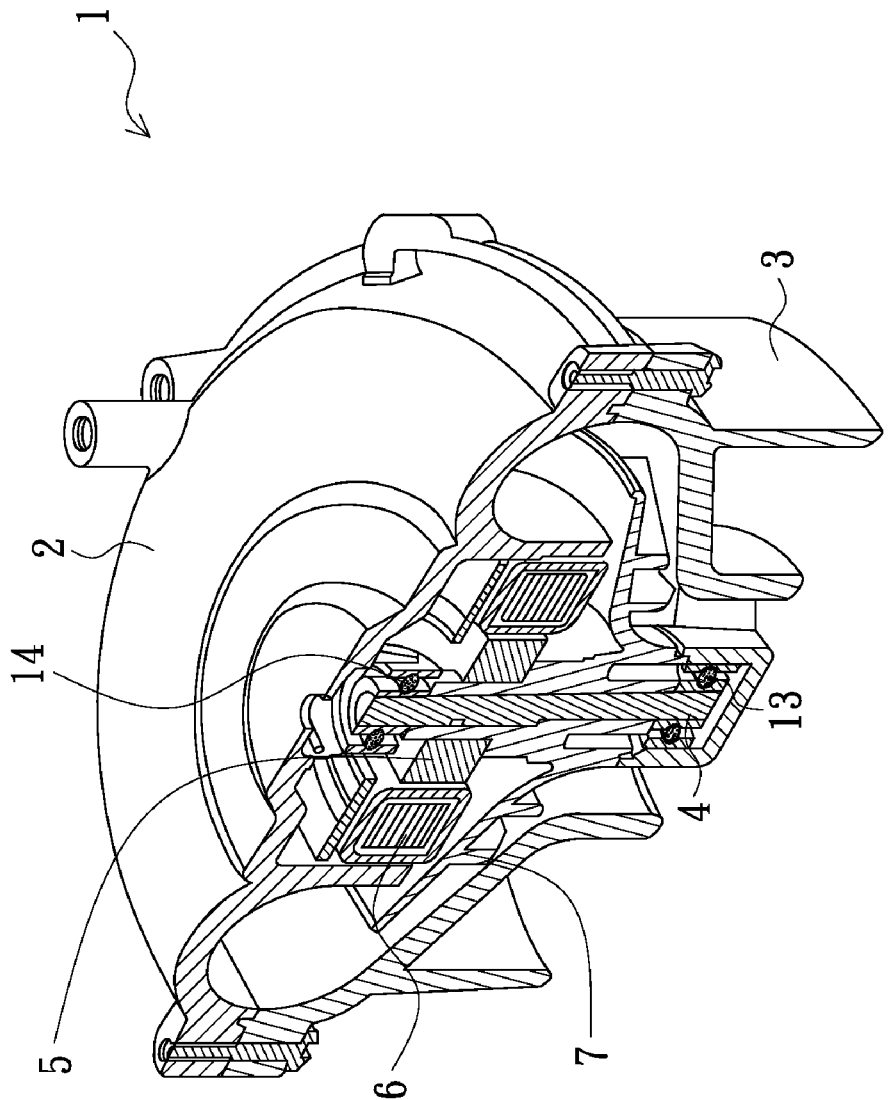
FIG. 1 is a three dimensional cross sectional view of a conventional brushless fan motor of a positive airway pressure breathing apparatus.
Figure 2:
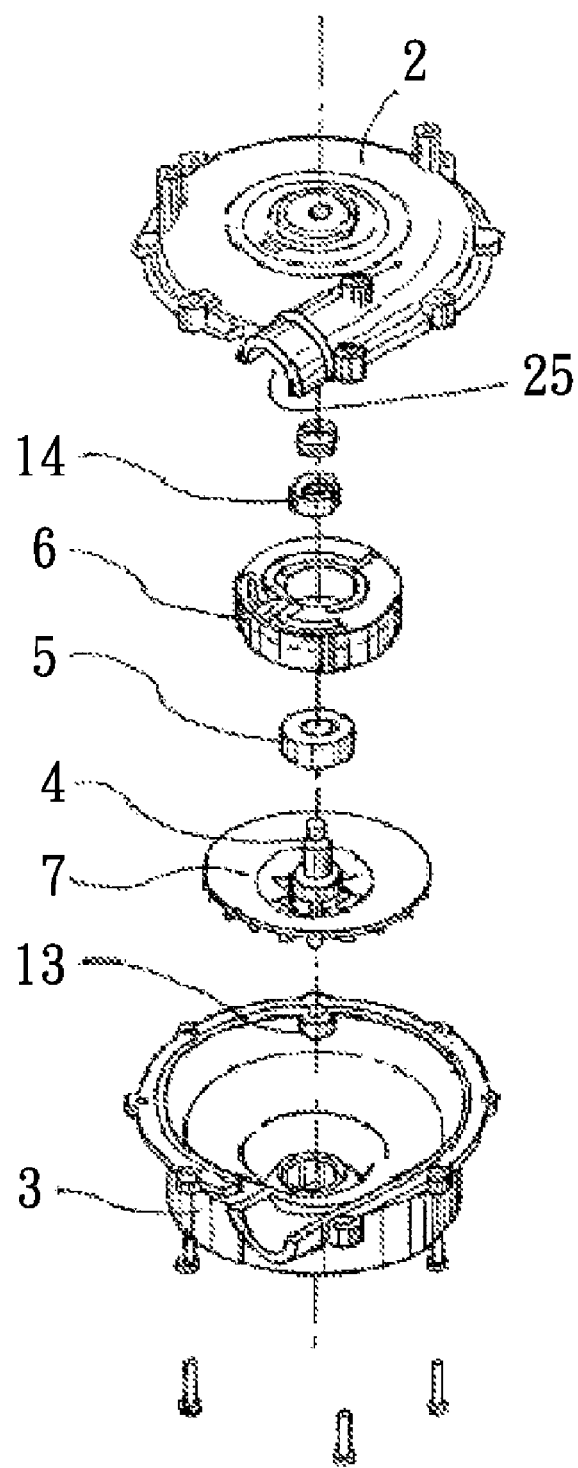
FIG. 2 is a three dimensional exploded view of FIG. 1.
Figure 3:
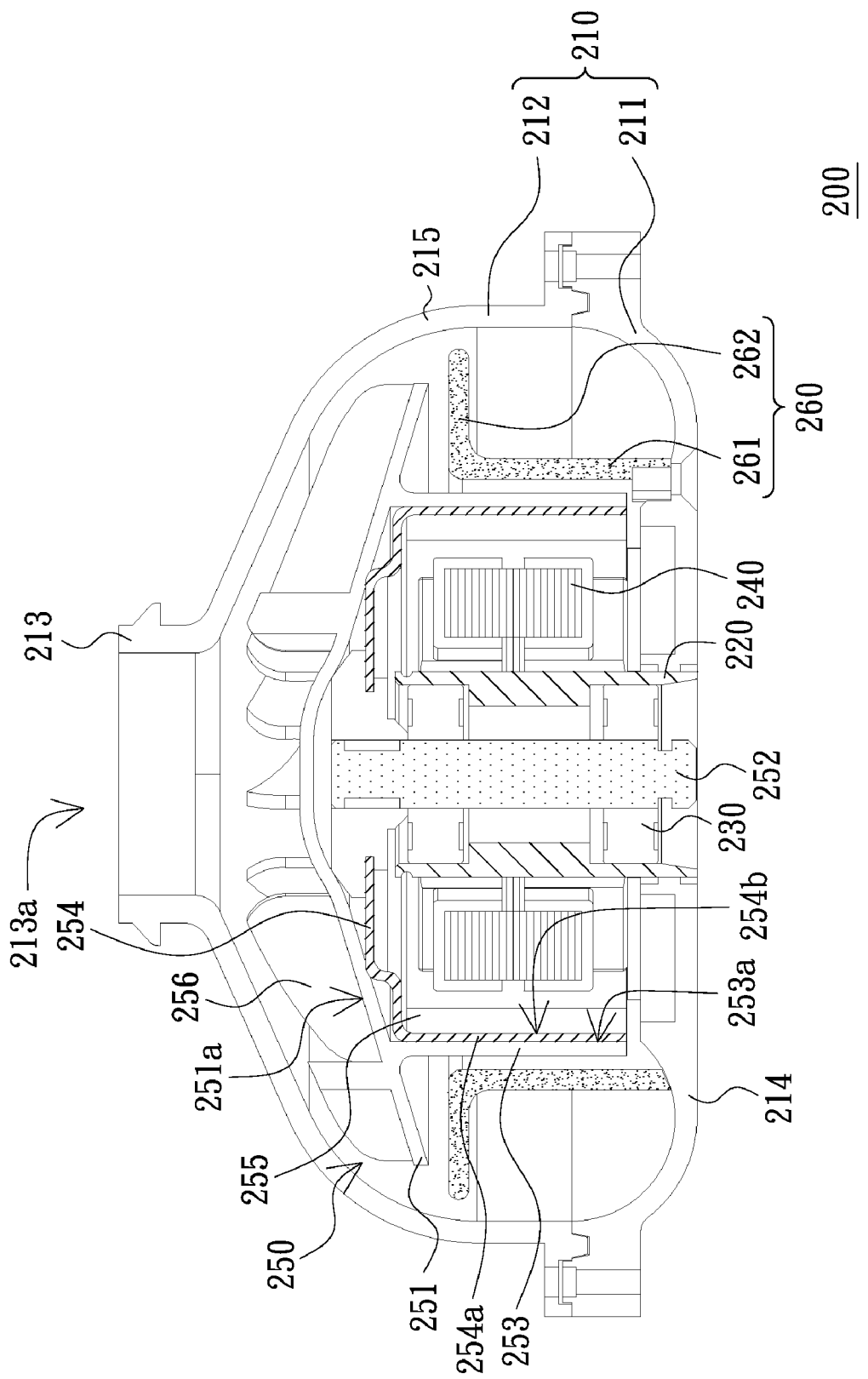
FIG. 3 is a schematic cross-sectional view of a brushless fan motor in accordance with an embodiment of the present invention.
Figure 4:
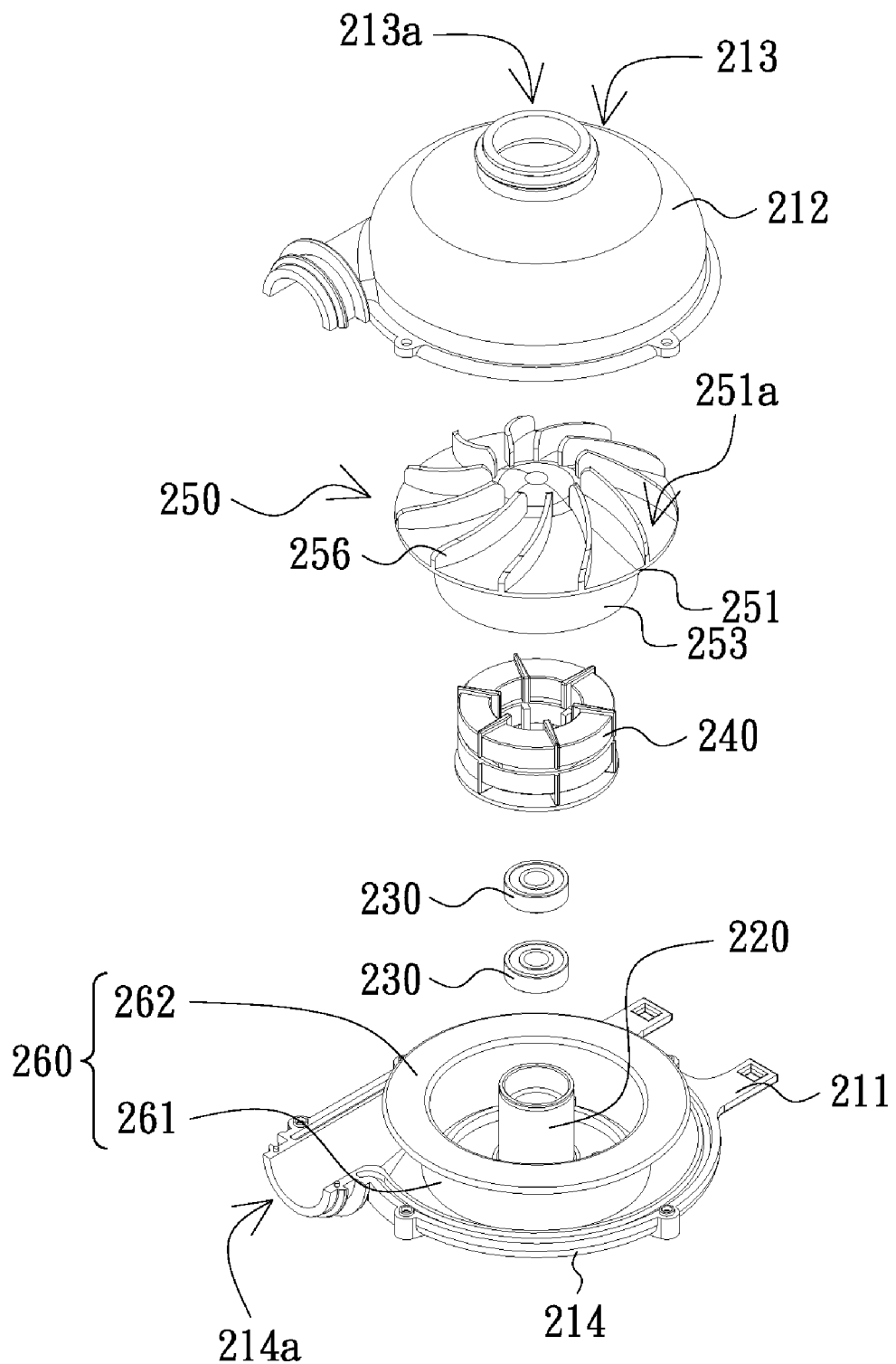
FIG. 4 is a schematic three dimensional exploded view of FIG. 3.

FIG. 3 is a schematic cross-sectional view of a brushless fan motor in accordance with an embodiment of the present invention, and FIG. 4 is a schematic three dimensional exploded view of FIG. 3. Referring to FIGS. 3 and 4, a brushless fan motor 200 of the present embodiment includes a case 210, a tubular part 220, at least a bearing 230, a toric coil 240 and a rotating assembly 250, wherein the tubular part 220, the bearing 230, the toric coil 240 and the rotating assembly 250 are disposed in the case 210. The case 210 has a top 213, a bottom 214 and a side wall 215 located between the bottom 214 and the top 213. The top 213 of the case 210 has an inlet 213a disposed thereon, and the side wall 215 has an outlet 214a disposed thereon. In the present embodiment, the case 210, for example, includes a base 211 and a cover 212 combined with each other. The cover 212 includes the top 213, the base 211 includes the bottom 214, and the side wall 215 and the outlet 214a are composed of a portion of the base 211 and a portion of the cover 212.

An end of the tubular part 220 is fixed at the bottom 214 of the case 210. The at least a bearing 230 is disposed in the tubular part 220. In the present embodiment, two bearings 230 are taken as an example, and the bearings 230 are, for example, respectively disposed at two ends of the tubular part 220. The toric coil 240 surrounds the tubular part 220. The brushless fan motor 200 of the present embodiment is, for example, a slotless motor.

Furthermore, the rotating assembly 250 includes a turntable 251, a rotating shaft 252, a loading ring 253, a permeability metal element 254 and a toric radial magnet 255. The turntable 251 has a top surface 251a facing the top 213 of the case 210 and a plurality of fan blades 256 disposed on the top surface 251a. The rotating shaft 252 is disposed through the bearing 230, and an end of the rotating shaft 252 is connected to the turntable 251. The turntable 251, the toric coil 240 and the rotating shaft 252 have the same central axis. The loading ring 253 is connected to the turntable 251 and surrounds the toric coil 240. The turntable 251 and the loading ring 253 can be, but not limited to, integrated into one piece. Besides, the permeability metal element 254 has an annular part 254a fixed at an inner wall 253a of the loading ring 253. The toric radial magnet 255 is fixed at an inner wall 254b of the annular part 254a of the permeability metal element. That is, the permeability metal element 254 and the toric radial magnet 255 also surround the toric coil 240, and the permeability metal element 254, the toric radial magnet 255 and the toric coil 240 have the same central axis.

In the present embodiment, when a current is applied to the toric coil 240, an induced electromagnetic field is generated to rotate the rotating assembly 250. When the fan blades 256 on the turntable 251 are rotated, air is guided into the case 210 from the inlet 213a and then output from the outlet 214a.

In the brushless fan motor 200 of the present embodiment, the bearings 230 are fixed at the tubular part 220 which is fixed at the bottom 214 of the case 210, so the bearings 230 have the same central axis even if assembling tolerance is existed between the base 211 and the cover 212 of the case 210. Such that, an eccentric rotation of the rotating shaft 252 can be avoided so as to reduce noise of the brushless fan motor 200 of the present embodiment.

It should be noted that to further reduce noise, the brushless fan motor 200 can further include a flow guiding member 260. The flow guiding member 260 is fixed at the bottom 214 of the case 210 and surrounds the loading ring 253 of the rotating assembly 250. More specifically, the flow guiding member 260 for example, includes a toric side wall 261 and a toric platform 262. The toric side wall 261 surrounds the loading ring 253 of the rotating assembly 250, and a bottom end of the toric side wall 261 is fixed at the bottom 214 of the case 210. The toric platform 262 extended from a top end of the toric side wall 261 toward outside of the toric side wall 261. Such that, the air flowing into the case 210 from the inlet 213a can flow to the outlet 214a through a flow channel between the flow guiding member 260 and the case 210 so as to prevent the air from contacting the rotating assembly 250 which is in high speed rotation and enhance pressure stability in the case 210, thereby reducing noise of the brushless fan motor 200. Furthermore, the flow guiding member 260 can prevent the rotating assembly 250 from being impacted by foreign objects such as particles.

Figure 5:
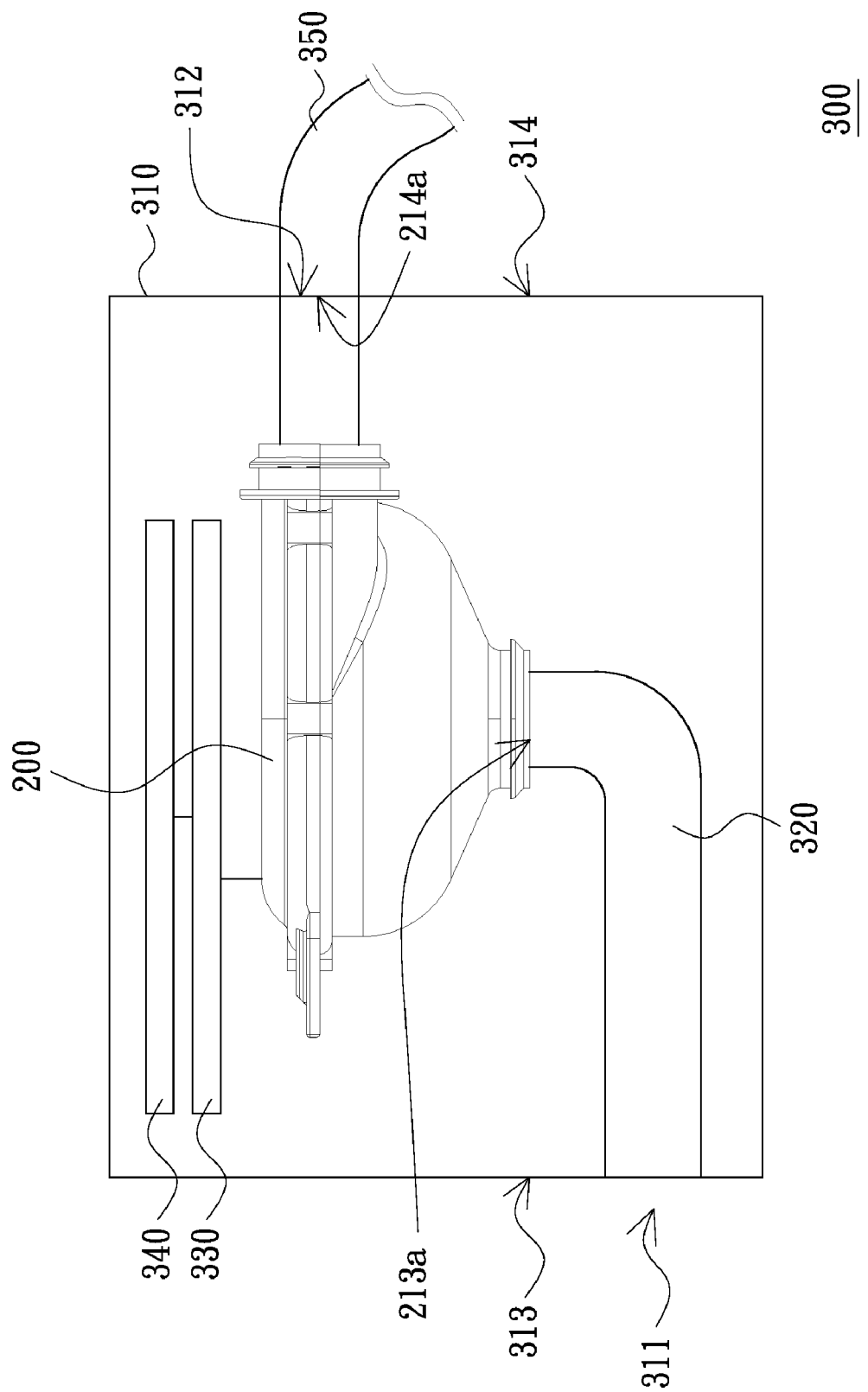
FIG. 5 is a schematic view of a positive airway pressure breathing apparatus in accordance with an embodiment of the present invention.

FIG. 5 is a schematic view of a positive airway pressure breathing apparatus in accordance with an embodiment of the present invention. Referring to FIG. 5, a positive airway pressure breathing apparatus 300 of the present embodiment includes a box 310, the above-mentioned brushless fan motor 200, a power control module 330 and a circuit board assembly 340. The box 310 has a fist air hole 311 and a second air hole 312. The fist air hole 311 and the second air hole 312 are, for example, disposed at two opposite side walls 313 and 314 of the box 310. The circuit board assembly 340, the power control module 330 and the brushless fan motor 200 are disposed in the box 310. The circuit board assembly 340 is electrically connected to the power control module 330, and the power control module 330 is electrically connected to the brushless fan motor 200. The inlet 213a of the brushless fan motor 200 is, for example, communicated with the fist air hole 311 through a conducting pipe 320, and the outlet 214a is communicated with the second air hole 312. The air from the fist air hole 311 can enters the brushless fan motor 200 through the inlet 213a, and then flows to outside through the outlet 214a and the second air hole 312. The outlet 214a or the second air hole 312 can be connected with another conducting pipe 350. The air from the outlet 214a can flow to a mask through the conducting pipe 350 so as to be used by a user wearing the mask.

Referring to FIGS. 4 and 5, the circuit board assembly 340 can control the power control module 330 to provide a suitable current to the toric coil 240 according to various relative rotation angles between the toric radial magnet 255 and the toric coil 240 so as to drive the rotating assembly 250 to rotate. The driving method is known by one skilled in the art, and detailed description for the driving method is omitted.

In summary, in the present invention, each bearing is disposed at the tubular part which is fixed at the bottom of the case, thereby preventing a central axis of the bearing from being tilted. Such that, an eccentric rotation of the rotating shaft can be avoided so as to reduce noise of the brushless fan motor and the positive airway pressure breathing apparatus using the brushless fan motor. Furthermore, in one embodiment, the flow guiding member not only can enhance pressure stability in the case to further reduce noise, but also can prevent the rotating assembly from being impacted by foreign objects.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A brushless fan motor, comprising:
   a case having a top, a bottom and a side wall located between the bottom and the top, the top having an inlet disposed thereon, and the side wall having an outlet disposed thereon;
   a tubular part disposed in the case, and an end of the tubular part is fixed at the bottom;
   at least a bearing disposed in the tubular part;
   a toric coil surrounding the tubular part; and
   a rotating assembly, comprising:
      a turntable having a top surface facing the top of the case and a plurality of fan blades disposed on the top surface;
      a rotating shaft disposed through the bearing, and an end of the rotating shaft being connected to the turntable;
      a loading ring connected to the turntable and surrounding the toric coil;
      a permeability metal element having an annular part fixed at an inner wall of the loading ring; and
      a toric radial magnet fixed at an inner wall of the annular part of the permeability metal element.

2. The brushless fan motor according to claim 1, wherein the case comprises a base and a cover, the cover comprises the top, the base comprises the bottom, and the side wall and the outlet are composed of a portion of the base and a portion of the cover.

3. The brushless fan motor according to claim 1, wherein the turntable and the loading ring are integrated into one piece.

4. The brushless fan motor according to claim 1, further comprising a flow guiding member fixed at the bottom of the case and surrounding the loading ring of the rotating assembly.

5. The brushless fan motor according to claim 4, wherein the flow guiding member comprises:
   a toric side wall surrounding the loading ring of the rotating assembly, and a bottom end of the toric side wall is fixed at the bottom of the case; and
   a toric platform extended from a top end of the toric side wall toward outside of the toric side wall.

6. A positive airway pressure breathing apparatus, comprising:
   a box having a fist air hole and a second air hole;
   a brushless fan motor disposed in the box, wherein the brushless fan motor comprises:
      a case having a top, a bottom and a side wall located between the bottom and the top, the top having an inlet disposed thereon, the side wall having an outlet disposed thereon, the inlet being communicated with the fist air hole, and the outlet being communicated with the second air hole;
      a tubular part disposed in the case and an end of the tubular part being fixed at the bottom;
      at least a bearing disposed in the tubular part;
      a toric coil surrounding the tubular part; and
      a rotating assembly, comprising:
         a turntable having a top surface facing the top of the case and a plurality of fan blades disposed on the top surface;
         a rotating shaft disposed through the bearing, and an end of the rotating shaft being connected to the turntable;
         a loading ring connected to the turntable and surrounding the toric coil;
         a permeability metal element having an annular part fixed at an inner wall of the loading ring; and
         a toric radial magnet fixed at an inner wall of the annular part of the permeability metal element;
   a power control module disposed in the box and electrically connected to the brushless fan motor; and
   a circuit board assembly disposed in the box and electrically connected to the power control module.

7. The positive airway pressure breathing apparatus according to claim 6, wherein the case comprises a base and a cover, the cover comprises the top, the base comprises the bottom, and the side wall and the outlet are composed of a portion of the base and a portion of the cover.

8. The positive airway pressure breathing apparatus according to claim 6, wherein the turntable and the loading ring are integrated into one piece.

9. The positive airway pressure breathing apparatus according to claim 6, wherein the brushless fan motor further comprises a flow guiding member fixed at the bottom of the case and surrounding the loading ring of the rotating assembly.

10. The positive airway pressure breathing apparatus according to claim 9, wherein the flow guiding member comprises:
   a toric side wall surrounding the loading ring of the rotating assembly, and a bottom end of the toric side wall is fixed at the bottom of the case; and
   a toric platform extended from a top end of the toric side wall toward outside of the toric side wall.

* * * * *